United States Patent [19]

Petersen et al.

[11] Patent Number: 4,840,954
[45] Date of Patent: Jun. 20, 1989

[54] 6,7-DISUBSTITUTED 1-CYCLOPROPLY-1,4-DIHYDRO-4-OXO-1,8-NAPHTHYRIDINE-3-CARBOXYLIC ACIDS

[75] Inventors: Uwe Petersen, Leverkusen; Klaus Grohe, Odenthal; Hans-Joachim Zeiler, Velbert; Karl G. Metzger, Wuppertal, all of Fed. Rep. of Germany

[73] Assignee: Bayer Aktiengesellschaft, Leverkusen, Fed. Rep. of Germany

[21] Appl. No.: 815,440

[22] Filed: Dec. 31, 1985

[30] Foreign Application Priority Data

Jan. 10, 1985 [DE] Fed. Rep. of Germany ....... 3500562
Mar. 13, 1985 [DE] Fed. Rep. of Germany ....... 3508816

[51] Int. Cl.$^4$ .................. A61K 31/41; A61K 31/436; C07D 471/04
[52] U.S. Cl. .................. 514/254; 514/300; 544/362; 546/123
[58] Field of Search .................. 546/123; 544/362; 514/254, 300

[56] References Cited

U.S. PATENT DOCUMENTS

| | | | |
|---|---|---|---|
| 4,292,317 | 9/1981 | Pesson | 544/363 |
| 4,341,784 | 7/1982 | Matsumoto | 546/123 |
| 4,359,578 | 11/1982 | Matsumoto | 546/123 |
| 4,448,962 | 5/1984 | Irikura | 544/363 |
| 4,544,658 | 10/1985 | Peterson | 544/363 |
| 4,563,459 | 1/1986 | Grohe | 544/363 |
| 4,571,396 | 2/1986 | Hutt | 546/156 |
| 4,616,019 | 10/1986 | Chu | 546/123 |
| 4,649,144 | 3/1987 | Matsumoto | 546/123 |
| 4,663,457 | 5/1987 | Mich | 546/123 |
| 4,665,079 | 5/1987 | Culbertson | 546/123 |

FOREIGN PATENT DOCUMENTS

| | | | |
|---|---|---|---|
| 0078362 | 5/1983 | European Pat. Off. | |
| 0106489 | 4/1984 | European Pat. Off. | |
| 0132845 | 2/1985 | European Pat. Off. | |
| 0153163 | 8/1985 | European Pat. Off. | |
| 0153163 | 8/1985 | European Pat. Off. | |
| 0153828 | 9/1985 | European Pat. Off. | |
| 0160578 | 11/1985 | European Pat. Off. | 546/123 |
| 0089480 | 5/1985 | Japan | 546/123 |
| 0126284 | 7/1985 | Japan | 546/123 |

OTHER PUBLICATIONS

Chemical Abstracts, (103) 1985, p. 581, Ref. Nr. 22617d; Columbus, Ohio, U.S.
Chemical Abstracts, JP-A-60 32 790 (Dainippon Pharm. Co., Ltd.) 02/19/1985, *Zusammenfassung*.
Pro-Drugs as Novel Druge Delivekry Systems, American Chem Society Sep. 10, 1984, p. 380.

*Primary Examiner*—Robert J. Warden
*Assistant Examiner*—Robert Benson
*Attorney, Agent, or Firm*—Sprung Horn Kramer & Woods

[57] ABSTRACT

New 6,7-disubstituted-1-cyclopropyl-1,4-dihydro-4-oxo-1,8-naphthyridine-3-carboxy lic acids of the formula (I)

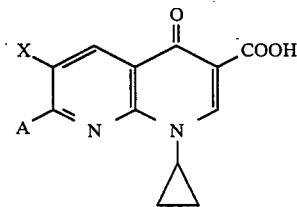

in which X represents halogen or nitro and A represents

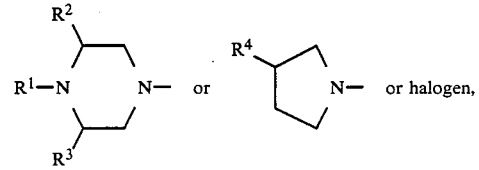

wherein $R^1$, $R^2$, $R^3$ and $R^4$ are defined hereinbelow are disclosed as well as their usefulness as antibacterial agents.

12 Claims, No Drawings

6,7-DISUBSTITUTED 1-CYCLOPROPLY-1,4-DIHYDRO-4-OXO-1,8-NAPHTHYRIDINE-3-CARBOXYLIC ACIDS

The present invention relates to new 6,7-disubstituted 1-cyclopropyl-1,4-dihydro-4-oxo-1,8-naphthyridine-3-carboxylic acids, processes for their preparation and antibacterial agents and feed additives containing these compounds.

It has been found that the new 6,7-disubstituted 1-cyclopropyl-1,4-dihydro-4-oxo-1,8-naphthyridine-3-carboxylic acids of the formula (I)

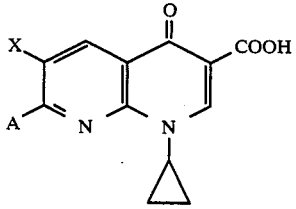 (I)

in which
X represents halogen or nitro and
A represents

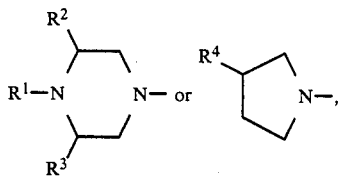

or halogen, in particulr chlorine or fluorine,
wherein
$R^1$ represents hydrogen, a branched or straight-chain alkyl group with 1 to 4 carbon atoms, which can optionally be substituted by a hydroxyl or methoxy group, a phenacyl radical which is optionally substituted by hydroxyl, methoxy, chlorine or fluorine, an oxoalkyl radical with 2 to 4 carbon atoms, 4-aminobenzyl, formyl or acetyl, or
represents the radical

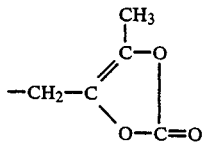

$R^2$ represents hydrogen or methyl, or phenyl or thienyl which is optionally substituted by chlorine, fluorine, methyl, hydroxyl or methoxy,
$R^3$ represents hydrogen or methyl and
$R^4$ represents hydrogen, hydroxyl, amino, alkyl- or dialkyl-amino with 1 or 2 carbon aotms in the alkyl group, hydroxymethyl, aminomethyl or alkyl- or dialkyl-aminomethyl with 1 or 2 carbon atoms in the alkyl group, and pharmaceutically usable hydrates, acid addition salts and alkali metal, alkaline earth metal, silver and guanidinium salts thereof, and in the form of their esters and in the other customary pro-drug forms, have a powerful antibacterial action.

They are therefore suitable as active compounds for human medicine and veterinary medicine, veterinary medicine also including the treatment of fish for therapy or prevention of bacterial infections.

Preferred compounds of the formula (I) are those
in which
X represents chlorine or fluorine and
A represents

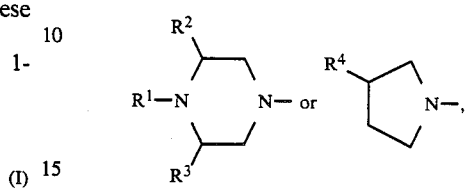

or halogen,
in particular chlorine or fluorine,
wherein
$R^1$ represents hydrogen, a branched or straight-chain alkyl group with 1 to 3 carbon atoms, which can optionally be substituted by a hydroxyl group, or a phenacyl radical which is optionally substituted by chlorine or fluorine, an oxoalkyl radical with 3 or 4 carbon atoms, 4-aminobenzyl, formyl or acetyl,
$R^2$ represents hydrogen or methyl, or phenyl which is optionally substituted by chlorine or fluorine,
$R^3$ represents hydrogen or methyl and
$R^4$ represents hydrogen, hydroxyl, amino, aminomethyl, methylaminomethyl, ethylaminomethyl or diethylaminomethyl.

Particularly preferred compounds of the formula (I) are those
in which
X represents chlorine or fluorine and
A represents

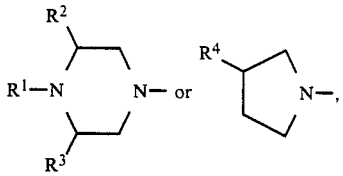

or halogen,
in particular chlorine or fluorine,
wherein
$R^1$ represents hydrogen, methyl, ethyl, 2-hydroxyethyl, phenacyl, 2-oxopropyl, 3-oxobutyl or formyl,
$R^2$ represents hydrogen, methyl or phenyl,
$R^3$ represents hydrogen or methyl and
$R^4$ represents hydrogen, amino, aminomethyl, ethylaminomethyl or diethylaminomethyl.

The compounds of the formula (I) in the form of their methyl, ethyl, pivaloyloxymethyl, pivaloyloxyethyl or (5-methyl-2-oxo-1,3-dioxol-4-yl-methyl) esters are moreover preferred.

It has furthermore been found that the compounds of the formula (I) are obtained by a process in which the 1-cyclopropyl-7-halogeno-1,4-dihydro-4-oxo-1,8-naphthyridine-3-carboxylic acids of the formula (II)

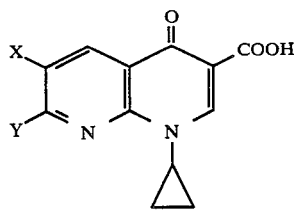 (II)

in which
X has the abovementioned meaning and
Y represents halogen, preferably chlorine or fluorine,
are reacted with amines of the formula (III)

A—H in which
A has the abovementioned meaning, if appropriate in the presence of acid-binding agents (method A).

Compounds of the formula (I) according to the invention can also be obtained by a process in which 1-cyclopropyl-1,4-dihydro-4-oxo-7-(1-piperazinyl)-1,8-naphthyridine-3-carboxylic acids of the formula (IV)

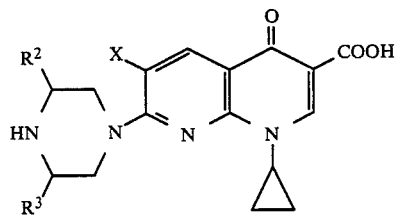 (IV)

in which
X, $R^2$ and $R^3$ have the abovementioned meaning, are reacted with compounds of the formula (V)

$R^1$—Z     (V)

in which
$R^1$ has the abovementioned meaning, but cannot be hydrogen, and
Z denotes halogen, in particular chlorine, bromine or iodine, acyloxy, ethoxy or hydroxyl, if appropriate in the presence of acid-binding agents (method B).

Compounds of the formula (I) ($R^1$=CH₃—CO—CH₂CH₂—) according to the invention are also obtained by a process in which a compound of the formula (IV) is reacted with methyl vinyl ketone of the formula (VI)

CH₃—CO—CH=CH₂     (VI)

(method C).

If 2-methylpiperazine and 7-chloro-1-cyclopropyl-6-fluoro-1,4-dihydro-4-oxo-1,8-naphthyridine-3-carboxylic acid are used as starting substances in the reaction according to method A, the course of the reaction can be represented by the following equation:

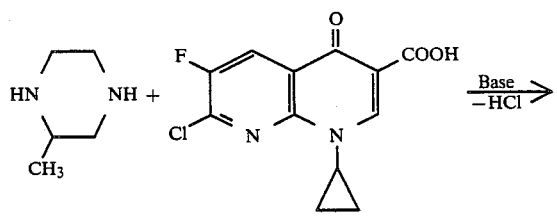

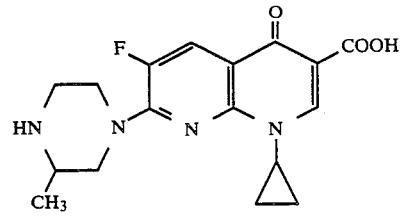

If, for example, chloroacetone and 6-chloro-1-cyclopropyl-1,4-dihydro-4-oxo-7-(1-piperazinyl)-1,8-naphthyridine-3-carboxylic acid are used as starting substances in the reaction according to method B, the course of the reaction can be represented by the following equation:

CH₃—CO—CH₂—Cl +

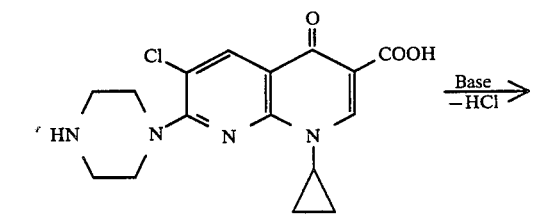

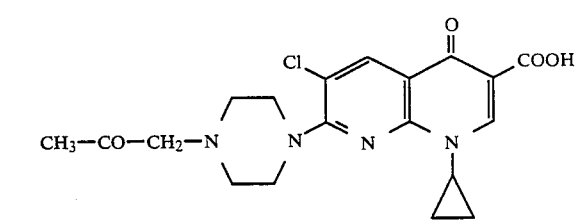

If, for example, methyl vinyl ketone and 1-cyclopropyl-6-fluoro-1,4-dihydro-4-oxo-7-(1-piperazinyl)-1,8-naphthyridine-3-carboxylic acid are used as starting compounds according to method C, the course of the reaction can be represented by the following equation:

CH₃—CO—CH=CH₂ +

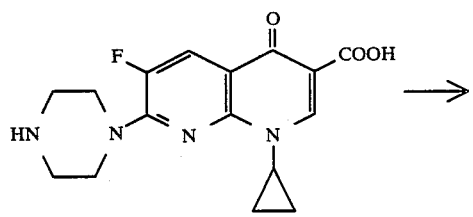

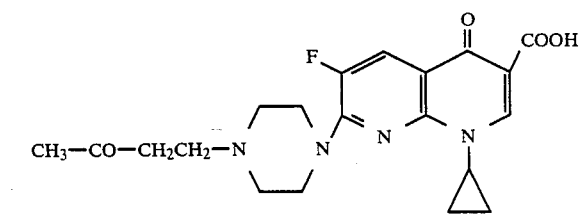

The 1-cyclopropyl-7-halogeno-1,4-dihydro-4-oxo-1,8-naphthridine-3-carboxylic acids of the formula (II) used as starting substances according to method A can be prepared in accordance with the following equation:

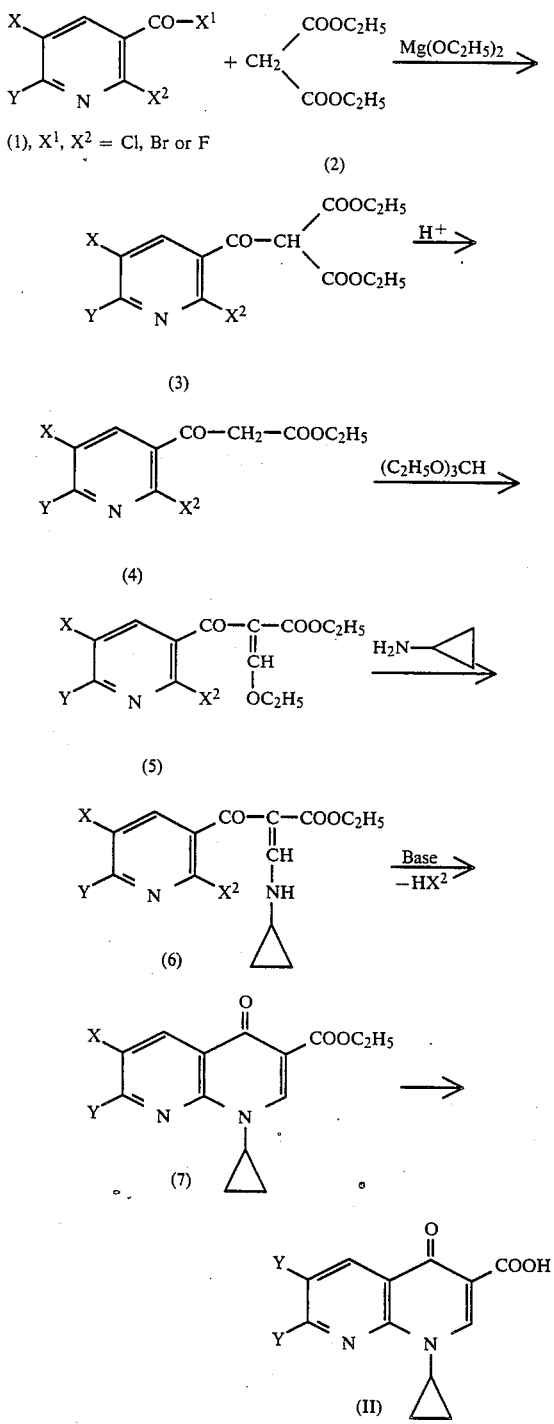

(1), $X^1$, $X^2$ = Cl, Br or F

According to this reaction, diethyl malonate (2) is acylated with the corresponding nicotinic acid halide (1) in the presence of magnesium ethylate to give the acylmalonate (3) (Organicum, 3rd edition 1964, page 438).

Partial hydrolysis and decarboxylation of (3) in an aqueous medium with catalytic amounts of sulfuric acid or 4-toluenesulfonic acid gives a good yield of the ethyl acylacetate (4), which is converted into the ethyl 2-(nicotinoyl)-3-ethoxy-acrylate (5) with triethyl orthoformate/acetic anhydride. Reaction of (5) with cyclopropylamine in a solvent, such as, for example, methylene chloride, an alcohol, chloroform, cyclohexane or toluene, leads to the desired intermediate product (6) in a slightly exothermic reaction.

The cyclization reaction (6)→(7) is carried out in a temperature range of about 60° to 300° C., preferably 80° to 180° C.

Diluents which can be used are dioxane, dimethylsulfoxide, N-methylpyrrolidone, sulfolane, hexamethylphosphoric acid trisamide and, preferably, N,N-dimethylformamide.

Possible acid-binding agents for this reaction stage are potassium tert.-butanolate, butyl-lithium, lithiumphenyl, phenyl-magnesium bromide, sodium methylate, sodium hydride and sodium or potassium carbonate. Potassium fluoride or sodium fluoride are particularly preferred if hydrogen fluoride has to be split off. It may be advantageous to employ an excess of 10 mol % of base.

The ester hydrolysis of (7) under basic or acid conditions carried out in the last step leads to the 1-cyclopropyl-7-halogeno-1,4-dihydro-4-oxo-1,8-naphthyridine-3-carboxylic acids (II).

The 2,5,6-trichloropyridine-3-carboxylic acid chloride [Helv. Chim. Acta 59, 222 (1976)] used as the starting substance for this synthesis route is already known. 2,6-Dichloro-5-fluoro-pyridine-3-carboxylic acid chloride can be obtained by the following route: 5-amino-2,6-dichloro-3-methylpyridine [Helv. Chim. Acta 59, 190 (1976)] is converted into 2,6-dichloro-5-fluoro-3-methylpyridine via 2,6-dichloro-3-methyl-5-(3,3-dimethyl-1-triazeno)-pyridine or by a Baltz-Schiemann reaction. This product is chlorinated to give 2,6-dichloro-5-fluoro-3-trichloromethyl-pyridine. Subsequent hydrolysis with sulfuric acid gives the carboxylic acid, which is converted into 2,6-dichloro-5-fluoro-pyridine-3-carboxylic acid chloride by the customary route. Alternatively, it is also possible to convert 5-fluoro-2,6-dihydroxy-pyridine-3-carboxamide [J. Amer. Chem. Soc. 101, 4423 (1979); J. Org. Chem. 46, 846 (1981)] into 2,6-dichloro-5-fluoro-pyridine-3-carbonitrile with phosphorus oxychloride and likewise to convert this product into the acid chloride, after hydrolysis to the carboxylic acid. Oxidation of 2,6-dichloro-3-chloromethyl-5-nitro-pyridine [Helv. Chim. Acta 59, 190 (1976)] gives the corresponding nicotinic acid, which gives 2,6-dichloro-5-nitro-pyridine-3-carboxylic acid chloride with thionyl chloride.

The amines of the formula (III) used as starting substances are known [U.S. No. 4,166,180 and J. Med. Chem. 26, 1116 (1983)]. Examples which may be mentioned are: piperazine, N-methylpiperazine, N-ethylpiperazine, N-(2-hydroxyethyl)-piperazine, N-(2-methoxyethyl)-piperazine, N-propylpiperazine, N-isopropylpiperazine, N-buytylpiperazine, N-(sec.-butyl)-piperazine, N-formylpiperazine, 2-methylpiperazine, cis- and trans-2,6-dimethylpiperazine, 2-phenylpiperazine, 2-(4-fluorophenyl)-piperazine, 2-(4-chlorophenyl)-piperazine, 2-(4-methylphenyl)-piperazine, 2-(4-methoxyphenyl)-piperazine, 2-(4-hydroxyphenyl)-piperazine, 2-(2-thienyl)-piperazine, pyrrolidine, 3-amino-pyrrolidine, 3-aminomethyl-pyrrolidine, 3-methylaminomethyl-pyrrolidine, 3-dimethylaminomethyl-pyrrolidine, 3-ethylaminomethyl-pyrrolidine and 3-hydroxy-pyrrolidine.

The compounds of the formula (V) used as starting substances are known. Examples which may be mentioned are: methyl iodide, methyl bromide, ethyl iodide, ethyl bromide, 2-hydroxyethyl chloride, 3-hydroxypropyl chloride, n-propyl bromide, isopropyl iodide, n-butyl bromide, sec.-butyl iodide, isobutyl bromide, formic acid/acetic acid anhydride, ethyl formate, formic acid, acetic anhydride and acetyl chloride.

The reaction of (II) with (III) according to method A is preferably carried out in a diluent, such as dimethylsulfoxide, N,N-dimethylformamide, hexamethyl-phosphoric acid trisamide, sulfolane, water, an alcohol, such as methanol, ethanol, n-propanol, isopropanol or glycol monomethyl ether, or pyridine. Mixtures of these diluents can also be used.

Acid-binding agents which can be used are all the customary inorganic and organic acid-binding agents. These include, preferably, the alkali metal hydroxides, alkali metal carbonates, organic amines and amidines. Acid-binding agents which may be specifically mentioned as being suitable are: triethylamine, 1,4-diazabicyclo[2,2,2]-octane (DABCO), 1,8-diaza-bicyclo[5,4,0]-undec-7-ene (DBU) or excess amine (III).

The reaction temperatures can be varied within a substancial range. In general, the reaction is carried out between about 20° and 200°C., preferably between 80° and 180°C.

The reaction can be carried out under normal pressure or under increased pressure. The reaction is in general carried out under pressures between about 1 and about 100 bar, preferably between 1 and 10 bar.

In carrying out the process according to the invention, 1 to 15 moles, preferably 1 to 6 moles, of the amine (III) are employed per mole of the carboxylic acid (II).

Free amino groups can be protected by a suitable amino-protective group, for example the t-butoxycarbonyl, ethoxycarbonyl or acetyl group, during the reaction, and liberated again after the reaction has ended. An aromatic amino group is introduced via reduction of a nitro group.

The reaction of (IV) with (V) is preferably carried out in a diluent, such as dimethylsulfoxide, dioxane, N,N-dimethylformamide, hexamethyl-phosphoric acid trisamide, sulfolane, water, an alcohol, such as methanol, ethanol, n-propanol, isopropanol or glycol monomethyl ether, or pyridine. Mixtures of these diluents can also be used.

Acid-binding agents which can be used are all the customary inorganic and organic acid-binding agents. These include, preferably, the alkali metal hydroxides, alkali metal carbonates, organic amines and amidines. Acid-binding agents which may be mentioned specifically as being particularly suitable are: triethylamine, 1,4-diazabicyclo[2,2,2]octane (DABCO) or 1,8-diazabicyclo[5,4,0]undec-7-ene (DBU).

The reaction temperatures can be varied within a substantial range. In general, the reaction is carried out between about 20° and about 180°C., preferably between 40° and 110°C.

The reaction can be carried out under normal pressure, but also under increased pressure. In general, the reaction is carried out under pressures between about 1 and about 100 bar, preferably between 1 and 10 bar.

In carrying out the process of method B according to the invention, 1 to 4 moles, preferably 1 to 1.5 moles, of the compound (V) are employed per mole of the compound (IV).

The reaction of (IV) with (VI) (method C) is preferably carried out in a diluent, such as dioxane, dimethylsulfoxide, N,N-dimethylformamide, methanol, ethanol, isopropanol, n-propanol or glycol monomethyl ether, or in mixtures of these diluents.

The reaction temperatures can be varied within a substantial range. In general, the reaction is carried out between about 20°C. and about 150°C., preferably between 50°C. and 100°C.

The reaction can be carried out under normal pressure, but also under increased pressure. In general, the reaction is carried out under pressures between about 1 and about 100 bar, preferably between 1 and 10 bar.

In carrying out the process of method C according to the invention, 1 to 5 moles, preferably 1 to 2 moles, of the compound (VI) are employed per mole of the compound (IV).

The acid addition salts of the compounds according to the invention are prepared in the customary manner, for example by dissolving the betaine in excess aqueous acid and precipitating the salt with a water-miscible organic solvent (methanol, ethanol, acetone or acetonitrile). It is also possible to heat equivalent amounts of betaine and acid in water until a solution is obtained and then to evaporate the solution to dryness. Pharmaceutically usable salts are to be understood as, for example, the salts of hydrochloric acid, sulfuric acid, acetic acid, glycolic acid, lactic acid, succinic acid, citric acid, tartaric acid, methanesulfonic acid, galacturonic acid, gluconic acid, glutamic acid and asparaginic acid.

The alkali metal or alkaline earth metal salts are obtained, for example, by dissolving the betaine in less then the stoichiometric amount of alkali metal or alkaline earth metal hydroxide solution, filtering off the undissolved betaine and evaporating the filtrate to dryness. Sodium, potassium or calcium salts are pharmaceutically suitable. the corresponding silver salts of the 1,4-dihydro-4-oxo-1,8-naphthyridine-3-carboxy-lic acids are obtained by reacting an alkali metal salt or alkaline earth metal salt with a suitable silver salt, such as silver nitrate.

New active compounds which may be mentioned specifically, in addition to the compounds listed in the examples, are: 1-cyclopropyl-6-fluoro-1,4-dihydro-7-(3,5-dimethyl-1-piperazinyl)-4-oxo-1,8-naphthyridine-3-carboxylic acid, 1-cyclopropyl-6-fluoro-1,4-dihydro-7-(4-isopropyl-1-piperazinyl)-4-oxo-1,8-naphthyridine-3-carboxylic acid, 7-(4-butyl-1-piperazinyl)-6-chloro-1-cyclopropyl-1,4-dihydro-4-oxo-1,8-naphthyridine-3-carboxylic acid, 1-cyclopropyl-6-fluoro-1,4-dihydro-4-oxo-7-(4-phenacyl-1-piperazinyl)-1,8-naphthyridine-3-carboxylic acid, 1-cyclopropyl-6-fluoro-1,4-dihydro-7-(3,4-dimethyl-1-piperazinyl)-4-oxo-1,8-naphthyridine-3-carboxylic acid hydrochloride, 1-cyclopropyl-6-fluoro-1,4-dihydro-7-[3-methyl-4-(2-oxopropyl)-1-piperazinyl]-4-oxo-1,8-naphthyridine-3-carboxylic acid, 6-chloro-1-cyclopropyl-1,4-dihydro-4-oxo-7-[4-(3-oxobutyl)-1-piperazinyl]-1,8-naphthyridine-3-carboxylic acid, 1-cyclopropyl-6-fluoro-7-(4-formyl-1-piperazinyl)-1,4-dihydro-4-oxo-1,8-naphthyridine-3-carboxylic acid, 7-(4-acetyl-1-piperazinyl)-1-cyclopropyl-6-fluoro-1,4-dihydro-4-oxo-1,8-naphthyridine-3-carboxylic acid, 6-chloro-1-cyclopropyl-1,4-dihydro-7-(1-piperazinyl)-4-oxo-1,8-naphthyridine-3-carboxylic acid, 6-chloro-1-cyclopropyl-1,4-dihydro-7-(4-methyl-1-piperazinyl)-4-oxo-1,8-naphthyridine-3-carboxylic acid, 6-chloro-1-cyclopropyl-1,4-dihydro-7-(3-methyl-1-piperazinyl)-4-oxo-1,8-naphthyridine-3-carboxylic acid, 6-chloro-1-cyclopropyl-7-(4-ethyl-1-piperazinyl)-1,4-dihydro-4-oxo-1,8-naphthyridine-3-carboxylic acid, 6-chloro-1-cyclopropyl-1,4-dihydro-4-oxo-7-[4-(3-oxopropyl)-1-piperazinyl]-1,8 -naphthyridine-3-carboxylic acid hydrochloride, 1-cyclopropyl-6-fluoro-7-[3-(4-fluorophenyl)-1-piperazinyl]-1,4-dihydro-4-oxo-1,8-naphthyridine-3-carboxylic acid, 6-chloro-1-cyclopropyl-1,4-dihydro-4-oxo-7-(3-phenyl-1-piperazinyl)-1,8-naphthyridine-3-carboxylic acid, 1-cyclopropyl-1,4-dihydro-6-nitro-4-oxo-7-(1-piperazinyl)-1,8-naphthyridine-3-carboxylic acid, 1-cyclopropyl-1,4-dihydro-7-(4-methyl-1-piperazinyl)-6-nitro-4-oxo-1,8-naphthyridine-3-carboxylic acid, 7-[4-(4-aminobenzyl)-1-piperazinyl]-1-cyclopropyl-1,4-dihydro-4-oxo-1,8-naphthyridine-3-carboxylic acid, 7-(3-amino-1-pyrrolidinyl)-1-cyclopropyl-1,4-dihydro-4-oxo-1,8-naphthyridine-3-carboxylic acid and 1-cyclopropyl-7-(3-ethylaminomethyl-1-pyrrolidinyl)-1,4-dihydro-4-oxo-1,8-naphthyridine-3-carboxylic acid.

This invention furthermore relates to compounds of the formula (VII)

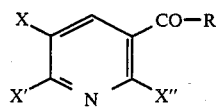

in which
X represents halogen or nitro,
X' and X" are identical or different and represent halogen, in particular chlorine or fluorine, and
R denotes OH, halogen, in particular chlorine, or alkoxycarbonylmethyl, with methyl or ethyl in the alkoxy part.

The following examples illustrate the invention:
Preparation of the starting compounds

EXAMPLE A 2,6-Dichloro-3-methyl-5-(3,3-dimethyl-1-triazeno)-pyridine

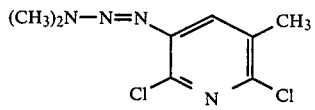

285 ml of half-concentrated hydrochloric acid are slowly added to 43 g (0.24 mole) of 5-amino-2,6-dichloro-3-methyl-pyridine (Helv. Chim. Acta 59, 190 [1976]), the mixture is cooled to 0°, a solution of 17.2 g (0.25 mole) of sodium nitrite in 70 ml of water is added dropwise and the mixture is subsequently stirred at 0° for some time. This diazonium salt solution is added dropwise to a solution of 150 g of sodium carbonate in 430 ml of water and 70 ml of 40-50% strength aqueous dimethylamine solution at 0°-3° in the course of 90 minutes and the mixture is subsequently stirred at 0°. The precipitate is filtered off with suction, rinsed thoroughly with water and dried under a high vacuum at 40° C.

Yield: 49.3 g (88% of theory), melting point: 91°-95° C.

EXAMPLE B 2,6-Dichloro-5-fluoro-3-methyl-pyridine

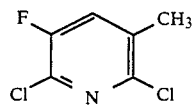

43.9 g (0.19 mole) of 2,6-dichloro-3-methyl-5-(3,3-dimethyl-1-triazeno)-pyridine are decomposed in 80 ml of hydrofluoric acid at 125°-135° C. in an autoclave. After distillation, a product is obtained which has a purity, determined by gas chromatography, of 87% and in addition also contains 12% of chlorine/fluorine replacement product. Yield: 19 g, boiling point: 81°-95°/18 mbar Melting point: 39°-41° C.

EXAMPLE C 2,6-Dichloro-5-fluoro-3-trichloromethyl-pyridine

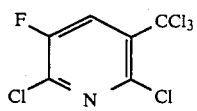

49.4 g (0.27 moles) of 2,6-dichloro-5-fluoro-3-methyl-pyridine are chlorinated at 120° C. for a total of about 20 hours, until the aliphatic proton is no longer detectable by NMR spectroscopy. The reaction mixture is distilled in a bulb tube distillation apparatus.

Yield: 61.7 g (80.6%), boiling point: 130°-150° C. (oven temperature)/0.4 mbar.

Mass spectrum: m/e 281 (M+), 246 (100%, M+—Cl), 211 (246-Cl) and 176 (211-Cl).

EXAMPLE D 2,6-Dichloro-5-fluoro-pyridine-3-carboxylic acid

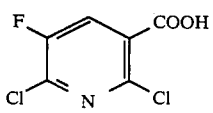

57 g (0.2 mole) of 2,6-dichloro-5-fluoro-3-trichloromethyl-pyridine are dissolved in 53 ml of 92% strength sulphuric acid and the mixture is stirred first at 25° C. for 45 minutes and then at 100° C. for 3 hours, until the evolution of hydrogen chloride has subsided. 24 g of 50% strength sulfuric acid are added and the mixture is heated at 100° C. for a further 6 hours. The reaction mixture is then cooled and poured onto ice and the precipitate is filtered off with suction, washed with water and dried.

Crude yield: 42 g (~100% of theory), melting point: 137°-149° C.; after recrystallisation from water: melting point: 154°-161° C.

Mass spectrum: m/e 209 (M+), 192 (M+—OH), 164 (192-CO), 129 (164-Cl) and 94 (129-Cl).

EXAMPLE E 2,6-Dichloro-5-fluoro-pyridine-3-carbonyl chloride

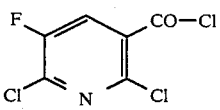

42 g (0.2 mole) of 2,6-dichloro-5-fluoro-pyridine-3-carboxylic acid are heated under reflux in a mixture of 43 g of thionyl chloride. 15 ml of dimethylformamide and 640 ml of toluene for 6 hours. The mixture is concentrated and the residue is distilled.

Yield: 33.8 g (74% of theory), boiling point 94°–98° C./1.3 mbar.

Mass spectrum: m/e 227 (M+), 192 (100%, M+—Cl) and 164 (40%, M+—COCl).

EXAMPLE F

Ethyl (2,6-dichloro-5-fluoro-pyridine-3-carbonyl)-acetate

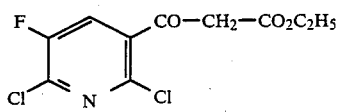

0.8 g of carbon tetrachloride is added to 3.7 g (0.15 mole) of magnesium filings in 9.3 ml of ethanol and, when the evolution of hydrogen has started, a mixture of 23.9 g (0.15 mole) of diethyl malonate, 18.5 ml of ethanol and 58 ml of toluene is added dropwise at 50°–60° C. The mixture is subsequently stirred at this temperature for 1 hour and cooled to −5° to −10° C. and a solution of 31 g (0.14 mole) of 2,6-dichloro-5-fluoro-pyridine-3-carbonyl chloride in 14.5 ml of toluene is slowly added dropwise. Thereafter, the mixture is stirred at 0° for 1 hour, brought to room temperature overnight and warmed at 40°–50° C. for a further 2 hours. A mixture of 60 ml of water and 9 ml of concentrated sulfuric acid is added to the reaction mixture, while cooling with ice, and the organic phase is separated off. The aqueous phase is extracted with toluene, the combined organic extract is washed with saturated sodium chloride solution and dried with sodium sulphate and the solvent is stripped off. 50.1 g of diethyl (2,6-dichloro-5-fluoro-pyridine-3-carbonyl)-malonate are obtained as a crude product. This product is heated under reflux for 10 hours, after addition of 50 ml of water and 0.1 g of 4-toluenesulfonic acid, the mixture is extracted with methylene chloride, the extract is dried with sodium sulphate and concentrated, the residue is stirred with a little ether and the crystals are isolated.

Yield: 14.3 g (34% of theory), melting point: 69°–72° C.

Mass spectrum: m/e 279 (M+), 244 (60%, M+—Cl), 216 (74%, 244-28), 192 (100%, C6HCl2FNO), 164 and 29.

According to the NMR spectrum (CDCl3), the compound is present virtually entirely as the enol.

EXAMPLE G

7-Chloro-1-cyclopropyl-6-fluoro-1,4-dihydro-4-oxo-1,8-naphthyridine-3-carboxylic acid

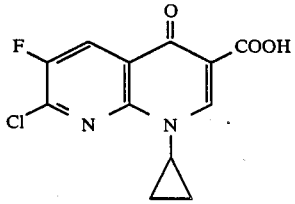

14 g (50 mmol) of ethyl (2,6-dichloro-5-fluoro-pyridine-3-carbonyl)-acetate are heated at 150°–160° C. with 11.1 g (75 mmol) of triethyl orthoformate in 13 g of acetic anhydride for 2 hours. The mixture is concentrated in vacuo and 15.6 g of ethyl 2-(2,6-dichloro-5-fluoro-pyridine-3-carbonyl)-3-ethoxyacrylate are obtained as an oily residue.

3 g of cyclopropylamine are added dropwise to 15.5 g (46 mmol) of this intermediate stage in 35 ml of ethanol, while cooling with ice, and the mixture is stirred at 20° C. for 1 hour. The product which has precipitated is filtered off with suction, washed with methanol and dried. 13.3 g of ethyl 2-(2,6-dichloro-5-fluoro-pyridine-3-carbonyl)-3-cyclopropylaminoacrylate of melting point 130°–133° C. (from ethanol) are obtained.

12.5 g (36 mmol) of ethyl 2-(2,6-dichloro-5-fluoro-pyridine-3-carbonyl)-3-cyclopropylamino-acrylate are heated at 100° C. in 75 ml of dimethylformamide with 6.5 g of potassium carbonate for 1 hour. The reaction mixture is poured onto ice-water and the product which has precipitated is filtered off with suction, washed with water and methanol and dried. 10.5 g (94% of theory) of ethyl 7-chloro-1-cyclopropyl-6-fluoro-1,4-dihydro-4-oxo-1,8-naphthyridine-3-carboxylate of melting point 176°–180° C. are obtained.

10.5 g (34 mmol) of this ester are heated at 150° C. in a mixture of 100 ml of acetic acid, 70 ml of water and 10 ml of concentrated sulfuric acid for 2 hours. The suspension is poured into 300 ml of ice-water and the precipitate is filtered off with suction, washed with water and methanol and dried in vacuo.

Yield: 7.85 g (82% of theory) of 7-chloro-1-cyclopropyl-6-fluoro-1,4-dihydro-4-oxo-1,8-naphthyridine-3-carboxylic acid of melting point 230°–233° C.

EXAMPLE H 6,7-Dichloro-1-cyclopropyl-1,4-dihydro-4-oxo-1,8-naphthyridine-3-carboxylic acid

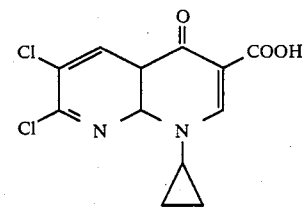

Ethyl (2,5,6-trichloropyridine-3-carbonyl)-acetate (melting point: 69°–71°; according to the 1H-NMR spectrum in denterochloroform, present as the enol to the extent of 50%) is prepared analogously to Example F starting from 2,5,6-trichloropyridine-3-carboxylic acid chloride [Helv. Chim. Acta 59, 222 (1976)]. This product is then converted analogously to Example G, via ethyl 6,7-dichloro-1-cyclopropyl-1,4-dihydro-4-oxo-1,8-naphthyridine-3-carboxylate (melting point: 176°–178°), into 6,7-dichloro-1-cyclopropyl-1,4-dihydro-4-oxo-1,8-naphthyridine-3-carboxylic acid, which, after recrystallisation from dimethylformamide, has a melting point of 243°–245°, with decomposition.

EXAMPLE 1

1-Cyclopropyl-6-fluoro-1,4-dihydro-4-oxo-7-(1-piperazinyl)-1,8-naphthyridine-3-carboxylic acid

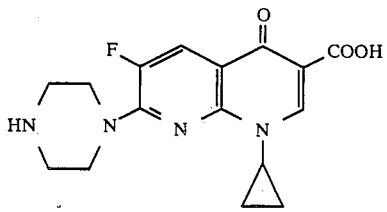

1.3 g (4 mmol) of 7-chloro-1-cyclopropyl-6-fluoro-1,4-dihydro-4-oxo-1,8-naphthyridine-3-carboxylic acid are heated at 110° C. in 8 ml of dimethylsulfoxide with 860 mg (10 mmol) of anhydrous piperazine for 15 minutes. The solvent is evaporated off in vacuo, the residue is boiled up with 5 ml of water (pH 7) and the precipitate is filtered off with suction, washed with water and boiled up with methanol.

Yield: 1.0 g (75% of theory), melting point: 278°–282° C. (with decomposition).

EXAMPLE 2

1-Cyclopropyl-6-fluoro-1,4-dihydro-7-(3-methyl-1-piperazinyl)-4-oxo-1,8-naphthyridine-3-carboxlyic acid

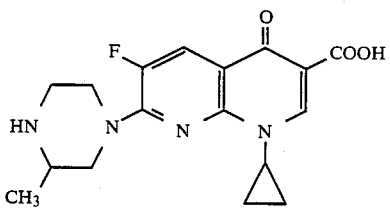

The procedure is analogous to Example 1, the reaction being carried out with 2-methylpiperazine at 100° C. for 15 minutes and the reaction product being recrystallised from glycol monomethyl ether.

Yield: 0.9 g (65% of theory), melting point: 243°–247° C. (with decomposition).

EXAMPLE 3

1-Cyclopropyl-6-fluoro-1,4-dihydro-7-(4-methyl-1-piperazinyl)-4-oxo-1,8-naphthyridine-3-carboxylic acid hydrochloride

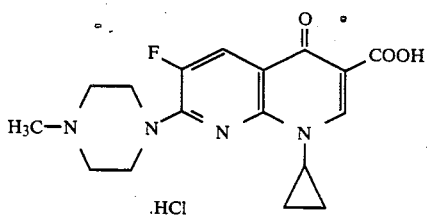

The procedure is analogous to Example 1, the reaction being carried out with N-methylpiperazine at 100° C. for 15 mintues and the reaction product being recrystallised from glycol monomethyl ether. The 1-cyclopropyl-6-fluoro-1,4-dihydro-4-oxo-7-(4-methyl-1-piperazinyl)-1,8-naphthyridine-3-carboxylic acid obtained (1.2 g of melting point 241°–244° C., with decomposition) is boiled up in a mixture of 20 ml of ethanol and 5 ml of 2N hydrochloric acid, and the hydrochloride formed is filtered off with suction, washed with ethanol and dried.

Yield: 1.1 g (72%), melting point: 305°–310° C. (with decomposition).

EXAMPLE 4

1-Cyclopropyl-7-(4-ethyl-1-piperazinyl)-6-fluoro-1,4-dihydro-4-oxo-1,8-naphthyridine-3-carboxylic acid hydrochloride

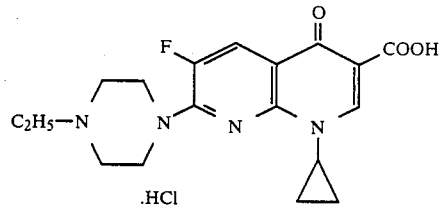

The reaction is carried out analogously to Example 3 with N-ethyl-piperazine at 100° C. for 30 minutes and the reaction product is then converted into the hydrochloride. Yield: 1.05 g (66% of theory), melting point: >300° C. (with decomposition).

EXAMPLE 5

1-Cyclopropyl-6-fluoro-1,4-dihydro-7-[4-(2-hydroxyethyl)-1-piperazinyl]-4-oxo-1,8-naphthyridine-3-carboxylic acid

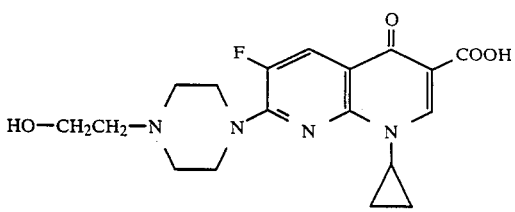

The reaction is carried out analogously to Example 1 with N-(2-hydroxyethyl)-piperazine at 100° C. for 30 minutes and the reaction product is recrystallised from glycol monomethyl ether.

Yield: 0.9 g (60% of theory), melting point: 241°–245° C. (with decomposition).

EXAMPLE 6

1-Cyclopropyl-6-fluoro-1,4-dihydro-4-oxo-7-(3-phenyl-1-piperazinyl)-1,8-naphthyridine-3-carboxylic acid

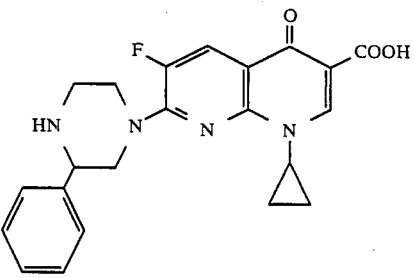

Analogously to Example 1, 810 mg (5 mmol) of 2-phenyl-piperazine are reacted in the presence of 1.8 g (8 mmol) of 1,4-diaza-bicyclo[2,2,2]octane (DABCO) at 100° C. for 30 minutes.

Yield: 0.85 g (42% of theory), melting point: 280°–283° C. (with decomposition).

EXAMPLE 7

1-Cyclopropyl-6-fluoro-1,4-dihydro-4-oxo-7-(1-pyrrolidinyl)-1,8-naphthyridine-3-carboxylic acid

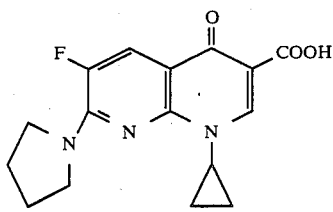

Analogously to Example 1, pyrrolidine is reacted at 100° C. for 30 minutes and the reaction product is recrystallised from dimethylformamide.

Yield: 70% of theory, melting point: 314°–316° C. (with decomposition).

EXAMPLE 8

1-Cyclopropyl-6-fluoro-1,4-dihydro-4-oxo-7-[4-(2-oxopropyl)-1-piperazinyl]-1,8-naphthyridine-3-carboxylic acid hydrochloride

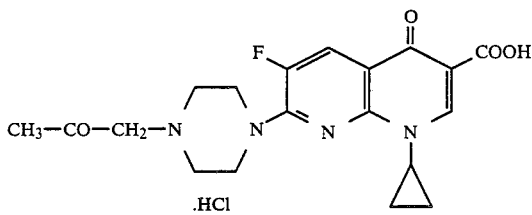

0.7 g (7.6 mmol) of chloroacetone and 1.05 g of triethylamine are added to 1.65 g (5 mmol) of 1-cyclopropyl-6-fluoro-1,4-dihydro-4-oxo-7-(1-piperazinyl)-1,8-naphthyridine-3-carboxylic acid in 25 ml of dimethylformamide and the mixture is heated at 80° C. for 3 hours. The suspension is concentrated in vacuo and the residue is stirred with 10 ml of water, filtered off with suction and dried. The product is heated in 15 ml of dilute hydrochloric acid (1:1), precipitated with ethanol, filtered off with suction and dried.

Yield: 1.5 g (71% of theory), melting point: >300° C. (with decomposition).

EXAMPLE 9

1-Cyclopropyl-6-fluoro-1,4-dihydro-4-oxo-7-[4-(3-oxobutyl)-1-piperazinyl]-1,8-naphthyridine-3-carboxylic acid hydrochloride

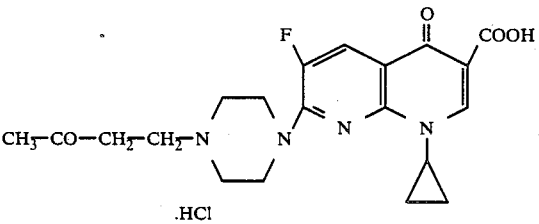

1.66 g (5 mmol) of the compound from Example 1 and 1.95 g (28 mmol) of methyl vinyl ketone are heated under reflux in 25 ml of ethanol for 7 hours, the precipitate obtained is dissolved in dilute hydrochloric acid (1:1) and the product is precipitated with ethanol.

Yield: 1.1 g (55% of theory), melting point: >300° C. (with decomposition).

EXAMPLE 10

6-Chloro-1-cyclopropyl-1,4-dihydro-7-(4-methyl-1-piperazinyl)-4-oxo-1,8-naphthyridine-3-carboxylic acid hydrochloride

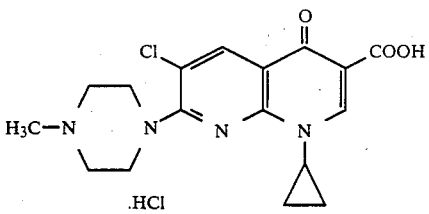

The procedure is analogous to Example 3, 6,7-dichloro-1-cyclopropyl-1,4-dihydro-4-oxo-1,8-naphthyridine-3-carboxylic acid and N-methyl-piperazine being used as starting compounds.

Yield: 66%, melting point: 304°–308° (with decomposition).

Examples of a tablet according to the invention

| Each tablet contains: | |
|---|---|
| Compound of Example 1 | 583.0 mg |
| Microcrystalline cellulose | 55.0 mg |
| Maize starch | 72.0 mg |
| Insoluble poly-(1-vinyl-2-pyrrolidone) | 30.0 mg |
| Highly disperse silicon dioxide | 5.0 mg |
| Magnesium stearate | 5.0 mg |
| | 750.0 mg |
| The lacquer shell contains: | |
| Poly-(O—hydroxypropyl-O—methyl)-cellulose 15 cp | 6.0 mg |
| Macrogol 4000 rec. INN (polyethylene glycols DAB) | 2.0 mg |
| Titanium(IV) oxide | 2.0 mg |
| | 10.0 mg |

The compounds according to the invention exhibit a broad antibacterial spectrum against Gram-positive and Gram-negative bacteria, in particular against Enterobacteriaceae, coupled with a low toxicity; in particular, they exhibit an action against those bacteria which are resistant towards various antibiotics, such as, for example, penicillins, cephalosporins, aminoglycosides, sulphonamides and tetracyclines.

These useful properties enable them to be used as chemotherapeutic active compounds in medicine and as substances for preserving inorganic and organic materials, in particular all types of organic materials, for example polymers, lubricants, paints, fibres, leather, paper and wood, and foodstuffs and water.

The compounds according to the invention are active against a broad spectrum of microorganisms. With their aid, it is possible to combat Gram-negative and Gram-positive bacteria and bacteria-like microorganisms, and the diseases caused by these pathogens can be prevented, alleviated and/or cured.

The compounds according to the invention are particularly active against bacteria and bacteria-like microorganisms. They are therefore particularly suitable, in human medicine and veterinary medicine, for the prophylaxis and chemotherapy of local and systemic infections caused by these pathogens.

For example, local and/or systemic diseases which are caused by the following pathogens or by mixtures of the following pathogens can be treated and/or prevented: Gram-positive cocci, for example Staphylococci (Staph. aureus and Staph. epidermidis) and Streptococci (Strept. agalactiae, Strept. faecalis, Strept. pneumoniae and Strept. pyogenes); Gram-negative cocci (Neisseria gonorrhoeae) and Gram-negative rod-shaped bacillae, such as Enterobacteriaceae, for example Escherichia coli, Haemophilus influenzae, Citrobacter (Citrob. freundii and Citrob. divernis), Salmonella and Shigella; and furthermore Klebsiellae (Klebs. pneumoniae and Klebs. oxytoca), Enterobacter (Ent. aerogenes and Ent. agglomerans), Hafnia, Serratia (Serr. marcescens), Proteus (Pr. mirabilis, Pr. rettgeri and Pr. vulgaris), Providencia, Yersinia and the genus Acinetobacter. The antibacterial spectrum moreover includes the genus Pseudomonas (Ps. aeruginosa and Ps. maltophilia) and strictly anaerobic bacteria, such as, for example, Bacteroides fragilis, representatives of the genus Peptococcus, Peptostreptococcus and the genus Clostridium, and furthermore Mykoplasma (M. pneumoniae, M. hominis and M. urealyticum) and Mycobacteria, for example Mycobacterium tuberculosis.

The above list of pathogens is purely illustrative and is no way to be interpreted as restrictive. Examples which may be mentioned of diseases which can be prevented, alleviated and/or cured by the compounds according to the invention are: otitis; pharyngitis; pneumonia; peritonitis; pyelonephritis; cystitis; endocarditis; systemic infections; bronchitis; arthritis; local infections; and septic diseases.

The present invention includes pharmaceutical formulations which, in addition to non-toxic, inert pharmaceutically suitable excipients, contain one or more compounds according to the invention, or which consist of one or more compounds according to the invention, as well as processes for the preparation of these formulations.

The present invention also includes pharmaceutical formulations in dosage units. This means that the formulations are in the form of individual parts, for example tablets, dragees, capsules, pills, suppositories and ampoules, of which the active compound content corresponds to a fraction or a multiple of an individual dose. The dosage units can contain, for example, 1, 2, 3 or 4 individual doses or ½, ⅓ or ¼ of an individual dose. An individual dose preferably contains the amount of active compound which is given in one administration and which usually corresponds to a whole, a half, a third or a quarter of a daily dose.

By non-toxic, inert pharmaceutically suitable excipients there are to be understood solid, semi-solid or liquid diluents, fillers and formulation auxiliaries of every kind.

Tablets, dragees, capsules, pills, granules, suppositories, solutions, suspensions and emulsions, pastes, ointments, gels, creams, lotions, powders and sprays may be mentioned as preferred pharmaceutical formulations.

Tablets, dragees, capsules, pills and granules can contain the active compound or compounds alongside the customary excipients, such as (a) fillers and extenders, for example starches, lactose, sucrose, glucose, mannitol and silica, (b) binders, for example carboxymethylcellulose, alginates, gelatine and polyvinylpyrrolidone, (c) humectants for example glycerol, (d) disintegrating agents, for example agar-agar, calcium carbonate and sodium carbonate, (e) solution retarders, for example paraffin and (f) absorption accecelerators, for example quaternary ammonium compounds (g) wetting agents, for example cetyl alcohol and glycerol monostearate, (h) adsorbents, for example kaolin and bentonite, and (i) lubricants, for example talc, calcium stearate, magnesium stearate and solid polyethylene glycols, or mixtures of the substances listed under (a) to (i).

The tablets, dragees, capsules, pills and granules can be provided with the customary coatings and shells, optionally containing opacifying agents, and can also be of such composition that they release the active compound or compounds only, or preferentially, in a certain part of the intestinal tract, optionally in a delayed manner, examples of embedding compositions which can be used being polymeric substances and waxes.

The active compound or compounds, optionally together with one or more of the abovementioned excipients, can also be in microencapsulated form.

Suppositories can contain, in addition to the active compound or compounds, the customary water-soluble or water-insoluble excipients, for example polyethylene glycols, fats, for example cocoa fat, and higher esters (for example $C_{14}$-alcohol with $C_{16}$-fatty acid), or mixtures of these substances.

Ointments, pastes, creams and gels can contain, in addition to the active compound or compounds, the customary excipients, for example animal and vegetable fats, waxes, paraffins, starches, tragacanth, cellulose derivatives, polyethylene glycols, silicones, bentonites, silica, talc and zinc oxide, or mixtures of these substances.

Powders and sprays can contain, in addition to the active compound or compounds, the customary excipients, for example lactose, talc, silica, aluminium hydroxide, calcium silicate and polyamide powder, or mixtures of these substances. Sprays can additionally contain the customary propellants, for example chlorofluorohydrocarbons.

Solutions and emulsions can contain, in addition to the active compound or compounds, the customary excipients, such as solvents, solubilising agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, especially cottonseed oil, groundnut oil, maize germ oil, olive oil, castor oil and sesame oil, glycerol, glycerolformal, tetrahydrofurfuryl alcohol, polyethylene glycols and fatty acid esters of sorbitan, or mixtures of these substances.

For parenteral administration, the solutions and emulsions can also be in a sterile form which is isotonic with blood.

Suspensions can contain, in addition to the active compound or compounds, the customary excipients, such as liquid diluents, for example water, ethyl alcohol or propylene glycol, suspending agents, for example ethoxylated isostearyl alcohols, polyoxyethylene sorbitol esters and sorbitan esters, microcrystalline cellulose, aluminium metahydroxide, bentonite, agar-agar and tragacanth, or mixtures of these substances.

The formulation forms mentioned can also contain colorants, preservatives and additives which improve the odor and flavor, for example peppermint oil and eucalyptus oil, and sweeteners, for example saccharin.

The therapeutically active compounds should preferably be present in the abovementioned pharmaceutical formulations in a concentration of about 0.1 to 99.5, preferably of about 0.5 to 95% by weight of the total mixture.

The abovementioned pharmaceutical formulations can also contain other pharmaceutical active compounds in addition to the compounds according to the invention.

The abovementioned pharmaceutical formulations are prepared in the customary manner according to known methods, for example by mixing the active compound or compounds with the excipient or excipients.

The active compounds or the pharmaceutical formulations can be administered locally, orally, parenterally, intraperitoneally and/or rectally, preferably orally or parenterally, such as intravenously or intramuscularly.

In general, it has proven advantageous both in human medicine and in veterinary medicine to administer the active compound or compounds according to the invention in total amounts of about 0.5 to about 500, preferably 5 to 100 mg/kg of body weight every 24 hours, optionally in the form of several individual administrations, in order to achieve the desired results. An individual administration preferably contains the active compound or compounds according to the invention in amounts of about 1 to about 250, in particular 3 to 60 mg/kg of body weight. However, it may be necessary to deviate from the dosages mentioned, and in particular to do so as a function of the species and body weight of the subject to be treated, the nature and severity of the disease, the nature of the formation and of the administration of the medicament and the period of interval within which administration takes place.

Thus it can in some cases suffice to manage with less than the abovementioned amount of active compound, whilst in other cases the abovementioned amount of active compound must be exceeded. The particular optimum dosage and mode of administration of the active compounds can easily be determined by anyone skilled in the art on the basis of his expert knowledge.

The new compounds can be administered in the customary concentrations and formulations together with the feed or with feed formulations or with the drinking water. Infection by Gram-negative or Gram-positive bacteria can thereby be prevented, alleviated and/or cured, and a promotion in growth and an improvement in feed utilisation can thereby be achieved.

The MIC values of some of the compounds according to the invention are given in the following table.

As a comparison, the corresponding MIC values of 1-ethyl-6-fluoro-1,4-dihydro-4-oxo-7-(1-piperazinyl)-1,8-naphthyridine-3-carboxylic acid (AT 2266, enoxacin), which is known from European Patent Application 9,425, Japanese Patent Applications 81/45473 [C.A. 95, 115 597 (1981)] and 81/46811 [C.A. 95, 121 142 (1981)], from J. Med. Chem. 27, 292 (1984) or from J. Heterocycl. Chem. 21, 673 (1984), have been given, it being found that the compounds according to the invention are superior to the known compound.

TABLE 1

| Strain | MIC values (mcg/ml) | | | |
|---|---|---|---|---|
| | Example 1 | Example 2 | Example 3 | Enoxacin |
| E.coli 4418 | 0.03 | 0.03 | 0.06 | 0.25 |
| E.coli Neum. | ≦0.015 | ≦0.015 | ≦0.015 | 0.06 |
| E.Coli 455/7 | 4 | ·8 | 8 | 16 |
| Klebsiella 63 | 0.03 | ≦0.015 | ≦0.015 | 0.5 |
| Klebsiella 6179 | 0.125 | 0.125 | 0.03 | 2 |
| Proteus mir. 8175 | 0.125 | 0.25 | 0.25 | 0.25 |
| Proteus vulg. 1017 | 0.06 | 0.125 | 0.125 | 0.125 |
| Proteus morg. 11006 | 0.06 | 0.03 | 0.06 | 0.125 |
| Providencia 12012 | 0.03 | 0.125 | 0.06 | 0.25 |
| Serratia 16040 | 8 | 8 | 8 | 32 |

TABLE 1-continued

| Strain | MIC values (mcg/ml) | | | |
|---|---|---|---|---|
| | Example 1 | Example 2 | Example 3 | Enoxacin |
| Staphyloc. 1756 | 0.5 | 0.5 | 0.5 | 1 |
| Staphyloc. 133 | 0.5 | 0.5 | 0.5 | 1 |
| Pseudomonas W. | 0.125 | 1 | 1 | 2 |

Agar dilution test / Isosensitest medium

What is claimed is:

1. A 1-cyclopropyl-1,4-dihydro-4-oxo-1,8-naphthyridine-3-carboxylic acid of the formula

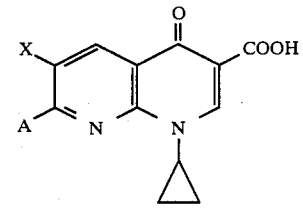

in which
X represents halogen and
A represents

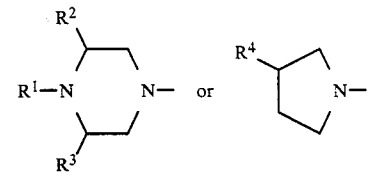

wherein
$R^1$ represents a branched or straight-chain alkyl group with 1 to 4 carbon atoms, which is substituted by a hydroxyl or methoxy group, a phenacyl radical which is optionally substituted by hydroxyl, methoxy, chlorine or fluorine, 2-oxopropyl, 3-oxobutyl or represents the radical

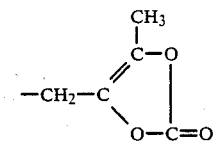

$R^2$ represents hydrogen or methyl, or phenyl or thienyl which is optionally substituted by chlorine, fluorine, methyl, hydroxyl, or methoxy,
$R^3$ represents hydrogen or methyl
$R^4$ represents hydroxymethyl and a pharmaceutically usable hydrate, acid addition salt and alkali metal, alkaline earth metal, silver and guanidinium salt thereof, and the methyl, ethyl, pivaloyloxymethyl, pivaloyloxyethyl or (5-methyl-2-oxo-1,3-dioxol-4-ylmethyl) esters thereof.

2. A 1-cyclopropyl-1,4-dihydro-4-oxo-1,8-naphthyridine-3-carboxylic acid according to claim 1, wherein
X represents chlorine or fluorine and
A represents

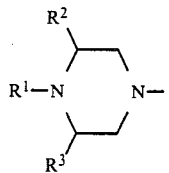

wherein
R¹ represents a branched or straight-chain alkyl group with 1 to 3 carbon atoms, which is substituted by a hydroxyl group, or a phenacyl radical which is optionally substituted by chlorine or fluorine, 2-oxopropyl or 3-oxobutyl or represents the radical

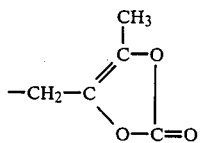

R² represents hydrogen or methyl, or phenyl which is optionally substituted or chlorine or fluorine, and
R³ represents hydrogen or methyl.

3. A 1-cyclopropyl-1,4-dihydro-4-oxo-1,8-naphthyridine-3-carboxylic acid according to claim 1,
wherein
X represents chlorine or fluorine and
A represents

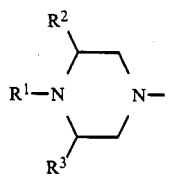

wherein
R¹ represents 2-hydroxyethyl, phenacyl, 2-oxopropyl, or 3-oxobutyl or represents

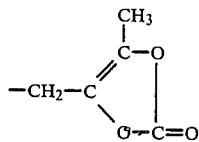

R² represents hydrogen, methyl or phenyl,
R³ represents hydrogen or methyl

4. A 1-cyclopropyl-1,4-dihydro-4-oxo-1,8-naphthyridine-3-carboxylic acid according to claim 1 which is 1-cyclopropyl-6-fluoro-1,4-dihydro-7-[4-(2-hydroxyethyl)-1-piperazinyl]-4-oxo-1,8-naphthyridine-3-carboxylic acid.

5. An antibacterial composition useful in the treatment of the human or animal body containing a bactericidally effective amount of a 1-cyclopropyl-1,4-dihydro-4-oxo-1,8-naphthyridine-3-carboxylic acid according to claim 1.

6. A method for preserving inorganic or organic materials by adding thereto an effective amount of a 1-cyclopropyl-1,4-dihydro-4-oxo-1,8-naphthyridine-3-carboxylic acid according to claim 1.

7. A method of combating bacterial infection wherein an effective amount of a 1-cyclopropyl-1,4-dihydro-4-oxo-1,8-naphthyridine-3-carboxylic acid according to claim 1 is administered to a human or animal body.

8. A 1-cyclopropyl-1,4-dihydro-4-oxo-1,8-naphthyridine-3-carboxylic acid of the formula

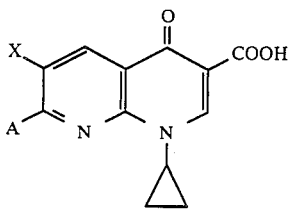

in which
X represents nitro and
A represents

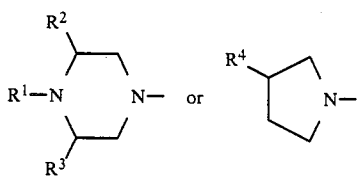

or halogen,
wherein
R¹ represents hydrogen, a branched or straight-chain alkyl group with 1 to 4 carbon atoms, which can optionally be substituted by a hydroxyl or methoxy group, a phenacyl radical which is optionally substituted by hydroxyl, methoxy, chlorine or fluorine, 2-oxopropyl, 3-oxobutyl, 4-aminobenzyl, formyl or acetyl, or represents the radical

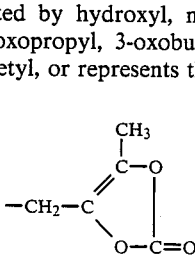

R² represents hydrogen or methyl, or phenyl or thienyl which is optionally substituted by chlorine, fluorine, methyl, hydroxyl or methoxy,
R³ represents hydrogen or methyl and
R⁴ represents hydrogen, hydroxyl, amino, alkyl- or dialkyl-amino with 1 or 2 carbon atoms in the alkyl group, hydroxymethyl, aminomethyl or alkyl- or dialkyl-aminomethyl with 1 or 2 carbon atoms in the alkyl group, and a pharmaceutically usable hydrate, acid addition salt and alkali metal, alkaline earth metal, silver and guanidinium salt thereof, and the methyl, ethyl, pivaloyloxymethyl, pivaloyloxyethyl or (5-methyl-2-oxo-1,3-dioxol-4-yl-methyl) esters thereof.

9. An antibacterial composition useful in the treatment of the human or animal body containing a bactericidally effective amount of a 1-cyclopropyl-1,4-dihydro-4-oxo-1,8-naphthyridine-3-carboxylic acid according to claim 8.

10. A method of combating bacteria wherein a bactericidally effective amount of a 1-cyclopropyl-1,4-dihydro-4-oxo-1,8-naphthyridine-3-carboxylic acid according to claim 8 is administered to a human or animal body.

11. A method for preserving inorganic or organic materials by adding thereto an effective amount of a 1-cyclopropyl-1,4-dihydro-4-oxo-1,8-naphthyridine-3-carboxylic acid according to claim 8.

12. A 1-cyclopropyl-1,4-dihydro-4-oxo-1,8-naphthyridine-3-carboxylic acid selected from the group consisting of 1-cyclopropyl-6-fluoro-1,4-dihydro-4-oxo-7-(4-phenacyl-1-piperazinyl)-1,8-naphthyridine-3-carboxylic acid, 1-cyclopropyl-6-fluoro-1,4-dihydro-7-[3-methyl-4-(2-oxo-propyl)-1-piperazinyl]-4-oxo-1,8-naphthyridine-3-carboxylic acid, 6-chloro-1-cyclopropyl-1,4-dihydro-4-oxo-7-[4-(3-oxobutyl)-1-piperazinyl-]-1,8-naphthyridine-3-carboxylic acid, 6-chloro-1-cyclopropyl-1,4-dihydro-4-oxo-7-[4-(3-oxo-propyl)1-piperazinyl-]-1,8-naphthyridine-3-carboxylic acid hydrochloride, 1-cyclopropyl-1,4-dihydro-6-nitro-4-oxo-7-(1-piperazinyl)-1,8-naphthyridine-3-carboxylic acid and 1-cyclopropyl-1,4-dihydro-7-(4-methyl-1-piperazinyl)-6-nitro-4-oxo-1,8-naphthyridine-3-carboxylic acid 1-cyclopropyl-1,4-dihydro-4-oxo-1,8-naphthyridine-3-carboxylic acid [,7-[4-(4-aminobenzyl)1-piperazinyl]-1-cyclopropyl-1,4-dihydro-4-oxo-1,8-naphthyridine-3-carboxylic acid, 7-(3-amino-1-pyrrolidinyl)-1-cyclopropyl-1,4-dihydro-4-oxo-1,8-naphthyridine-3-carboxylic acid and 1-cyclopropyl-7-(3-ethylaminomethyl-1-pyrrolidinyl)-1,4-dihydro-4-oxo-1,8-naphthyridine-3-carboxylic acid.

* * * * *

UNITED STATES PATENT AND TRADEMARK OFFICE
CERTIFICATE OF CORRECTION

PATENT NO. : 4,840,954

DATED : June 20, 1989

INVENTOR(S) : Uwe Petersen, et al

It is certified that error appears in the above-identified patent and that said Letters Patent is hereby corrected as shown below:

Title page:

| | |
|---|---|
| Abstract, line 2 | Correct --carboxylic-- |
| Col. 1, line 59 | Correct --atoms-- |
| Col. 3, line 15 | After "A-H" insert --(III)-- |
| Col. 3, line 65 | After "NH" delete "-" and substitute --+-- |
| Col. 19, line 28 | After "period" delete "of" and substitute --or-- |

Signed and Sealed this

Nineteenth Day of March, 1991

Attest:

HARRY F. MANBECK, JR.

Attesting Officer     Commissioner of Patents and Trademarks